United States Patent [19]

Hahn et al.

[11] Patent Number: 5,728,884
[45] Date of Patent: Mar. 17, 1998

[54] PROCESS FOR THE WORK-UP OF COMPLEX AMINE HYDROFLUROIDES

[75] Inventors: Ulrich Hahn, Frankfurt; Raimund Franz, Kelkheim; Günter Siegemund, Hofheim, all of Germany

[73] Assignee: Solvay, Belgium

[21] Appl. No.: 574,221

[22] Filed: Dec. 18, 1995

[30] Foreign Application Priority Data

Dec. 20, 1994 [DE] Germany .................... 44 45 529.1

[51] Int. Cl.⁶ .................................................. C07C 209/84
[52] U.S. Cl. ..................... 564/468; 524/497; 570/134; 570/164
[58] Field of Search ........................... 570/164, 134; 564/468, 497

[56] References Cited

U.S. PATENT DOCUMENTS 4,734,526  3/1988  Albert et al. .

FOREIGN PATENT DOCUMENTS 2127732  1/1995  Canada .
0 634 383  1/1995  European Pat. Off. .
WO 86/00294  1/1986  WIPO .

OTHER PUBLICATIONS

Franz, R., *J. Fluorine Chemistry* 15:423–434 (1980).

Olah et al. *Synthesis*, Dec. 1973 (pp.779–780).

Yoneda et al. Chemistry Letters pp. 1135–1136, 1983.

*Primary Examiner*—Brian M. Burn
*Attorney, Agent, or Firm*—Connolly & Hutz

[57] ABSTRACT

The invention relates to a process for the work-up of a liquid complex hydrofluoride of a tertiary amine of the formula (I) $[R^1R^2R^3N \cdot n\, HF]$, where the radicals $R^1$, $R^2$ and $R^3$ are $C_1$–$C_8$-alkyl groups which together have at least 7 carbon atoms and n is an integer or fractional number where $1.5<n<3$, which, for the purpose of molecular addition of HF to a halogenated alkene, is reacted with the latter. In the reaction of the halogenated alkene with the complex amine hydrofluoride of the formula (I), the molar ratio $HF:R^1R^2R^3N$ is allowed to fall until amine separates out as a further liquid phase, and the amine is separated off.

19 Claims, No Drawings

PROCESS FOR THE WORK-UP OF COMPLEX AMINE HYDROFLUROIDES

The present invention relates to a work-up process for complex amine hydrofluorides which are used for the molecular addition of hydrogen fluoride to halogenated alkenes.

German Patent Application P 43 39 539.2 which corresponds to U.S. Ser. No. 08/271,838 filed Jul. 7, 1994 abandoned describes a process for the molecular addition of hydrogen fluoride to halogenated alkenes by means of liquid complex hydrofluorides of organic nitrogen bases. The hydrofluorides used here are preferably complex hydrofluorides of the formula [A·n HF] having 2<n<3, in which A is a tertiary amine. Hydrofluorides of this type are known from, for example, J. Fluorine Chemistry 15 (1980), pp. 423–434 and are very easily obtained by reacting suitable amines with an amount of hydrogen fluoride corresponding to this formula. They react with halogenated alkenes, for example hexafluoropropene or trifluorochloroethylene, preferably at temperatures of from 0° to 100° C., with molecular addition of hydrogen fluoride to the halogenated alkenes occurring. After the distillative isolation of the addition product, the original composition of the complex hydrofluoride can be restored by reacting the reaction residue with hydrogen fluoride and the addition reaction can thus be repeated as often as desired.

The abovementioned patent application also describes a continuous procedure for the molecular addition of HF to gaseous halogenated alkenes in a bubble column with simultaneous feeding in of equivalent amounts of halogenated alkene and hydrogen fluoride to the liquid complex hydrofluoride. This can therefore be regarded and used as a continually reusable catalyst for the reaction of suitable halogenated alkenes with hydrogen fluoride.

However, when using "technical grade" hydrogen fluoride in said process, the impurities contained therein accumulate over the course of time in the complex hydrofluoride and can finally impair the conversion and the product quality. These impurities include, in particular, sulfur dioxide, sulfuric acid and fluorosilicic acid which react with complex hydrofluorides to form nonvolatile compounds. The liquid reactor contents therefore have to be replaced at certain time intervals and worked up in a manner which is as environmentally friendly as possible. However, such a work-up can also appear necessary for other reasons, e.g. in the case of a shut-down of a production plant.

It has now surprisingly been found when carrying out the abovementioned reaction of amine hydrofluorides with halogenated alkenes that when using complex hydrofluorides of certain tertiary amines having short-chain alkyl radicals, for example [(n-C$_3$H$_7$)$_3$N·2.9 HF] or [(n-C$_4$H$_9$)$_3$N·2.6 HF], a lowering of the HF/amine molar ratio to from about 1.5 to 2 leads to separation of a second, lower density, liquid phase which consists of virtually pure amine. The amount of the complex hydrofluoride decreases during the further course of the reaction in favor of the newly formed amine phase, which leads to an accumulation of the dissolved impurities in the hydrofluoride phase. An advantageous work-up of the complex hydrofluoride can be carried out in this manner, since the amine which separates can then be separated off and reused. The hydrofluoride phase containing a greater amount of impurities can, in contrast, be destroyed and the loss of amine and hydrogen fluoride can thus be reduced to a minimum.

The present invention accordingly provides a process for the work-up of a liquid complex hydrofluoride of a tertiary amine of the formula (I)

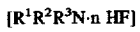   (I)

where the radicals $R^1$, $R^2$ and $R^3$ are identical or different and are straight-chain or branched $C_1$–$C_8$-alkyl groups which together have at least 7 carbon atoms and n is an integer or fractional number where 1.5<n<3, which, for the purpose of molecular addition of HF to a halogenated alkene of the formula (II)

   (II)

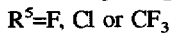

is reacted with this halogenated alkene, which comprises, in the reaction of the halogenated alkene of the formula (II) with the complex amine hydrofluoride of the formula (I), allowing the molar ratio HF:$R^1R^2R^3$N to fall until amine separates out as a further liquid phase, and separating off the amine.

The percentage of the amine present in the complex hydrofluoride (I) [$R^1R^2R^3$N·n HF] which separates out depends on the percentage of the HF present in (I) which is consumed by molecular addition to the halogenated alkene (II). The percentage of HF consumed can be controlled by setting a suitable mixing ratio of (I):(II). In a batchwise procedure, this mixing ratio is set prior to commencement of the reaction. In a continuous procedure, said mixing ratio is set during the reaction, namely by replacing only the halogenated alkene (II) consumed, but not the HF consumed.

In general, from 5 to 90% of the amine is allowed to separate out, preferably from 10 to 90%. It is easily possible to allow 100% of the amine to separate out by setting suitable mixing ratios of halogenated alkene (II): hydrofluoride (I) prior to the batchwise reaction or during the continuous reaction. A separation of 100% of said amine is, however, frequently not of interest.

The present work-up process is extraordinarily surprising. Although it is known to all those skilled in the art that hydrohalides of ammonia and organic amines are soluble in water and that the ammonia or the amine can be liberated by reacting these aqueous solutions with alkali, e.g. sodium hydroxide solution. However, the molecular addition of the hydrogen fluoride present in the complex amine hydrofluorides (I) to halogenated alkenes (II) is not carried out in water. It was therefore not at all to be expected that consumption of the HF would lead, long before reaching the stoichiometric HF/amine ratio of 1:1, to the separation of a further liquid phase consisting of pure amine.

The complex amine hydrofluorides of the formula (I) are preferably derived from the following tertiary amines $R^1R^2R^3$N: tri-n-propylamine, tri-n-butylamine, tri-n-pentylamine, triisopentylamine, tri-n-hexylamine, methyl-n-propyl-n-butylamine, methylisopropyl-n-butylamine. Particular preference is here given to tri-n-butylamine.

The halogenated alkenes of the formula (II) which are used are, in particular, the following: $CF_2$=$CF_2$, $CF_2$=$CClF$, $CF_2$=$CF$—$CF_3$, $CF_3$—$CF$=$CH$—$CF_3$, $CF_3$—$CF$=$C(CF_3)_2$, $C_2F_5$—$CF$=$C(CF_3)_2$, $C_2F_5CF$=$C(CF_3)(C_4F_9)$, but particularly $CF_2$=$CF$—$CF_3$ (hexafluoropropene).

The molecular addition of HF to these halogenated alkenes forms the following halogenated alkanes:

| Alkene (II) | Alkane |
|---|---|
| $CF_2=CF_2$ | $CF_3-CF_2H$ |
| $CF_2=CCIF$ | $CF_3-CHCIF$ |
| $CF_2=CF-CF_3$ | $CF_3-CHF-CF_3$ |
| $CF_3-CF=CH-CF_3$ | $CF_3-CF_2-CH_2-CF_3$ |
| $CF_3-CF=C(CF_3)_2$ | $CF_3-CF_2-CH(CF_3)_2$ |
| $C_2F_5-CF=C(CF_3)_2$ | $C_2F_5-CF_2-CH(CF_3)_2$ |
| $C_2F_5-CF=C(CF_3)(C_4F_9)$ | $C_2F_5-CF_2-CH(CF_3)(C_4F_9)$ |

It is also possible to use a mixture of two or more halogenated alkenes of the formula (II).

The work-up according to the invention of the complex hydrofluorides (I) used for the molecular addition of HF to halogenated alkenes (II) can be carried out under conditions and in apparatus which are the same as or similar to those of the addition reaction. Depending on the complex hydrofluoride used, the temperatures are generally from 0° to 150° C., preferably from 10° to 90° C., particularly preferably from 60° to 80° C.

The type of apparatus depends on whether the work-up is to be carried out batchwise or continuously, and also on the boiling points of the halogenated alkene (II) used and the halogenated alkane formed therefrom by HF addition and on the reactivity of the halogenated alkene.

In a batchwise procedure, it is possible to use, for example, stirred vessels provided with a reflux condenser, which vessels can, for the laboratory or pilot plant scale, also consist of borosilicate glass. When using low-boiling halogenated alkenes (II), the work-up process is advantageously carried out in closed pressure vessels fitted with a stirrer. When carrying out the work-up batchwise, the molar ratio of halogenated alkene (II):complex amine hydrofluoride (I) at the beginning of their reaction is generally selected so that from 5 to 90% of the amine present in the hydrofluoride (I), but preferably from 10 to 90% of the amine, separates out. After isolation of the halogenated alkane formed in the HF addition, the amine phase which has separated out is separated off and can be reconverted into the complex hydrofluoride (I).

The continuous HF addition to a gaseous halogenated alkene (II) is, as mentioned in the introduction, carried out with simultaneous feeding in of halogenated alkene and hydrogen fluoride to the complex hydrofluoride (I), e.g. in a bubble column. To work up the complex hydrofluoride, feeding in of hydrogen fluoride is interrupted with further feeding in of halogenated alkene. After the amine has separated out as a separate phase, it can be taken off (batchwise). The work-up can also be configured so as to be continuous, by feeding complex hydrofluoride (I) into the apparatus after interruption of the HF feed and continuously taking off the separated amine at the rate at which it is formed.

The use of bubble columns also allows the HF addition and the work-up of the complex hydrofluoride to be carried out simultaneously. This can be achieved, for example, by continuously taking off a small part of the complex hydrofluoride from the bubble column in which the HF addition proceeds and working up the complex hydrofluoride in a much smaller apparatus, or by two bubble columns of similar size forming a cascade, with the gaseous halogenated alkene first entering the first bubble column used for the work-up and the gas mixture formed there then being introduced into the second bubble column used for the HF addition.

The invention is illustrated by the following examples. The percentages are by weight unless otherwise indicated or obviously intended.

EXAMPLE 1

An autoclave fitted with a stirrer and having a capacity of 300 ccm was charged with 90 g (0.4 mol) of a complex hydrofluoride of tri-n-butylamine used for 800 operating hours in the molecular addition of hydrogen fluoride to hexafluoropropene. The hydrofluoride was homogeneous and liquid and had an HF/amine ratio of n=2.1. After closing the autoclave, 60 g of hexafluoropropene (0.4 mol) was injected from a pressure reservoir and the reaction mixture was stirred overnight at 50° C. Subsequently, after venting the autoclave, the low-boiling constituents were condensed in a trap cooled by dry ice. The yield of crude heptafluoropropane was 63.3 g (93% of theory) at a purity (according to the gas chromatogram) of 95%. The liquid residue in the autoclave weighed 83 g and consisted of two phases which were separated in a separating funnel. The lighter phase consisted of 31 g of tri-n-butylamine which, according to the gas chromatogram, had a purity of 98.8%; 52 g of complex hydrofluoride having an HF/amine ratio of n=1.9 were recovered as the heavier phase.

EXAMPLE 2

A glass reaction flask having a capacity of 250 ccm and fitted with a reflux condenser was charged with 45 g (0.2 mol) of a complex hydrofluoride of tri-n-butylamine which had an HF/amine ratio of n=2.60 g of perfluoro-(2-methyl-2-pentene) (0.2 mol) were then added dropwise and the mixture thus formed was stirred for 6 hours at from 50° to 60° C. The crude 2-trifluoromethyl-2-H-decafluoro-n-pentane formed by molecular addition of HF to the fluoropentene was subsequently distilled off at a boiling temperature of between 60° and 65° C. The yield was 60 g (93.8% of theory). The distillation residue consisted of two liquid phases which were separated in a separating funnel. The lighter phase consisted of 18 g of tri-n-butylamine which, according to the gas chromatogram, had a purity of 98%; 20 g of complex hydrofluoride having an HF/amine ratio of n=2 were recovered as the heavier phase.

EXAMPLE 3

A complex hydrofluoride of tri-n-butylamine which had been used for 1200 hours as medium and reagent for the molecular addition of hydrogen fluoride to hexafluoropropane now contained impurities which, according to elemental analysis, corresponded to a sulfur content of 0.1% and a silicon content of 0.03%. The HF/amine ratio in the used complex hydrofluoride (I) was 2, viz. [(n-$C_4H_9$)$_3$N·2 HF]. 200 g (0.89 mol) of this hydrofluoride were placed in a bubble column of borosilicate glass having a length of 70 cm and an internal diameter of 22 mm which could be heated from the outside, and the hydrofluoride was heated to 60° C. At this point in time, the liquid level of the hydrofluoride was 60 cm. At the bottom of the column, gaseous hexafluoropropene was introduced and finely distributed. Straight away, tri-n-butylamine which could easily be recognized by its light color separated out from the complex hydrofluoride as a lighter, second liquid phase whose volume increased at the expense of the hydrofluoride phase. The crude heptafluoropropane (raw gas) formed by molecular addition of HF to the hexafluoropropene left the top of the column and was condensed in a cold trap. From time to time, samples for gas-chromatographic analysis were taken from the raw gas stream.

At a liquid level of the hydrofluoride phase of 6 cm (corresponding to 10% of the initial value of 60 cm) a sample of this phase was taken and analyzed; the sulfur content was now 1.2% and the silicon content was 0.27%. Even at this low liquid level, the conversion of the hexafluoropropene was still above 50%. The tri-n-butylamine which had separated out as a second liquid phase (140 g) had an only pale yellow color and a purity of 98%.

We claim:

1. A process for the work-up of a impurities containing liquid complex hydrofluoride of a tertiary amine of the formula (I)

$$(R^1R^2R^3N \cdot n \, HF) \qquad (I)$$

where the radicals of $R^1$, $R^2$ and $R^3$ are identical or different and am straight-chain or branched $C_1$–$C_8$-alkyl groups which together have at least 7 carbon atoms and n is an integer or fractional number where $1.5<n<3$, comprising (a) reacting said complex hydrofluoride of formula (I) with a halogenated alkene of the formula (II)

$$R^4CF=CR^5R^6 \qquad (II)$$

wherein $R^4$ is F, $CF_3$ or $C_2F_5$ $R^5$ is F, Cl or $CF_3$ $R^6$ is H, F or perfluorinated $C_1$–$C_4$-alkyl, under such conditions that HF contained in the complex hydrofluoride of formula (I) is consumed by molecular addition to the halogenated alkene of formula (II), so inducing the formation of the two liquids phases, a first phase containing the remaining complex hydrofluoride and substantially all the impurities, and a further, lower density, liquid phase, which consists essentially of virtually pure amine;

(b) separating off said further, low density, liquid phase and (c) eliminating the phase containing the remaining complex hydrofluoride and the impurities accumulated therein.

2. The process as claimed in claim 1, wherein the work-up is carried out on a complex hydrofluoride of the formula (I) in which the amine $R^1R^2R^3N$ is tri-n-propylamine, tri-n-butylamine, tri-n-pentylamine, triisopentylamine, tri-n-hexylamine, methyl-n-propyl-n-butylamine or methylisopropyl-n-butylamine.

3. The process as claimed in claim 1, wherein the work-up is carried out on a complex hydrofluoride of the formula (I) in which the amine $R^1R^2R^3N$ is tri-n-butylamine.

4. The process as claimed in claim 1, wherein the work-up is carried out at a temperature of from 0° to 150° C.

5. The process as claimed in claim 1, wherein the work-up is carried out at a temperature of from 10° to 90° C.

6. The process as claimed in claim 1, wherein the work-up is carried out at a temperature of from 60° to 80° C.

7. The process as claimed in claim 1, wherein the complex hydrofluoride (I) is reacted batchwise with the halogenated alkene (II) and the molar ratio of halogenated alkene (II): complex amine hydrofluoride (I) at the beginning of their reaction is selected so that from 5 to 90% of the amine present in the hydrofluoride (I) separates out as a further liquid phase, and the amine is separated off.

8. The process as claimed in claim 7, wherein the molar ratio of halogenated alkene (II): complex amine hydrofluoride (I) is selected so that from 10 to 90% of the amine separates out.

9. The process as claimed in claim 1, wherein the work-up of the complex hydrofluoride (I) is carried out by reaction with a gaseous halogenated alkene (II) in a slender reactor and the amine which separates out as a separate phase is separated off.

10. The process as claimed in claim 9, wherein the amine which separates out is separated off continuously at the rate at which it is formed and is replaced by an equivalent amount of complex amine hydrofluoride (I).

11. The process as claimed in claim 9, wherein said slender reactor is a bubble column.

12. A process for the molecular addition of hydrogen fluoride to halogenated alkenes of formula (II)

$$R^4CF=CR^5R^6 \qquad (II)$$

wherein $R^4$ is F, $CF_3$ or $C_2F_5$ $R^5$ is F, Cl or $CF_3$ $R^6$ is H, F or perfluorinated $C_1$–$C_4$-alkyl, by reaction in the presence of a liquid complex hydrofluoride of a tertiary amine of the formula (I)

$$(R^1R^2R^3N \cdot n \, HF) \qquad (I)$$

where the radicals of $R^1$, $R^2$ and $R^3$ are identical or different and are straight-chain or branched $C_1$–$C_8$-alkyl groups which together have at least 7 carbon atoms and n is an integer or fractional number where $1.5<n<3$, comprising a work-up step wherein (a) the complex hydrofluoride of formula (I) is reacted with the halogenated alkene of the formula (II) under such conditions that HF contained in the complex hydrofluoride of formula (I) is consumed by molecular addition to the halogenated alkene of formula (II), so inducing the formation of the two liquid phases, a first phase containing the remaining complex hydrofluoride, and substantially all the impurities, and a further, lower density, liquid phase, which consists essentially of virtually pure amine;

(b) separating off said further, low density, liquid phase; and (c) reacting said separated liquid phase which consists essentially of virtually pure amine with HF to reconstitute the complex hydrofluoride of formula (I).

13. The process as claimed in claim 12, wherein in formula (I), the amine $R^1R^2R^3N$, is tri-n-propylamine, tri-n-butylamine, tri-n-pentylamine, triisopentylamine, tri-n-hexylamine, methyl-n-propyl-n-butylamine or methylisopropyl-n-butylamine.

14. The process as claimed in claim 13, wherein said amine is tri-n-butylamine.

15. The process as claimed in claim 12, wherein the complex hydrofluoride (I) is reacted batchwise with the halogenated alkene (II) and the molar ratio of halogenated alkene (II): complex hydrofluoride (I) at the beginning of their reaction is selected so that from 5 to 90% of the amine present in the hydrofluoride (I) separates out as a further liquid phase, and the amine is separated off.

16. The process as claimed in claim 15, wherein the molar ratio of halogenated alkene (II): complex hydrofluoride (I) is selected so that from 10 to 90% of the amines separates out.

17. The process as claimed in claim 12 wherein the complex hydrofluoride (I) is carried out by reaction with a gaseous halogenated alkene (II) in a slender reactor and the amine which separates out as a separate phase is separated off.

18. The process as claimed in claim 17, wherein the amine which separates out is separated off continuously at the rate at which it is formed and is replaced by an equivalent amount of complex amine hydrofluoride (I).

19. The process as claimed in claim 17, wherein the reaction is carried out at a temperature from 10° to 90° C.

* * * * *

UNITED STATES PATENT AND TRADEMARK OFFICE
CERTIFICATE OF CORRECTION

PATENT NO. : 5,728,884
DATED : March 17, 1998
INVENTOR(S) : Ulrich Hahn, Raimund Franz, Gunter Siegemund It is certified that error appears in the above-indentified patent and that said Letters Patent is hereby corrected as shown below:

At column 5, line 10, please delete "am straight-chain or" and insert --are straight-chain or --.

Signed and Sealed this

Twenty-first Day of July, 1998

Attest:

BRUCE LEHMAN

Attesting Officer          Commissioner of Patents and Trademarks